United States Patent [19]

Gefri et al.

[11] Patent Number: 4,704,480

[45] Date of Patent: Nov. 3, 1987

[54] PROCESS FOR THE PRODUCTION OF KETONES AND CARBINOLS

[75] Inventors: Fred J. Gefri, Hackettstown; Divakaran Masilamani, Morristown; Andiappan K. S. Murthy, Convent Station, all of N.J.

[73] Assignee: Allied Corporation, Morris Township, Morris County, N.J.

[21] Appl. No.: 892,545

[22] Filed: Aug. 4, 1986

[51] Int. Cl.$^4$ .............................................. C07C 45/73
[52] U.S. Cl. .................................... 568/396; 568/391; 568/881
[58] Field of Search ............... 568/396, 390, 391, 881, 568/388

[56] References Cited

U.S. PATENT DOCUMENTS

| | | | |
|---|---|---|---|
| 2,697,730 | 12/1954 | Mecorney et al. | 568/391 |
| 2,725,400 | 11/1985 | Mecorney et al. | 568/391 |
| 4,289,911 | 9/1981 | Isogai et al. | 568/396 |
| 4,599,453 | 7/1986 | Fragale et al. | 568/387 |
| 4,599,454 | 7/1986 | Elliott et al. | 568/387 |

*Primary Examiner*—James H. Reamer
*Attorney, Agent, or Firm*—Gale F. Matthews; Richard C. Stewart

[57] ABSTRACT

A novel process is described for the production of aliphatic ketones and an optional consequetive production of the corresponding carbinols. The starting reactants comprise ketones or aldehydes or compounds capable of converting to these in situ, such as alcohols. The reaction takes place in the presence of hydrogen in a selective temperature range, utilizing a catalyst comprising copper oxide.

20 Claims, No Drawings

PROCESS FOR THE PRODUCTION OF KETONES AND CARBINOLS

FIELD OF THE INVENTION

This invention relates to a novel process for the selective production of ketones and/or carbinols, with the capability of using the same catalyst and reactor.

BACKGROUND OF THE INVENTION

Ketones and alcohols have been produced from acetone through the use of various catalyst systems. German Pat. No. 2,023,512 describes an alternating catalyst layer system wherein the first layer is composed of $NiO$—$Cr_2O_3$ and the second, $MgO$, $SiO_2$, $Cr_2O_3$, $CuO$, $Al_2O_3$ and $CaO$. Japanese Pat. No. 75 00,644 describes the use of a catalyst containing Cu, ZnO and CrO to produce higher ketones from EtMeCHOH. M. Vendelin et al. Chem. Prum. 26(12), 634–8 (1976) discuss the synthesis of methylisobutylketone and diisobutylketone from acetone utilizing a $CuO$—$Cr_2O_3$—$BaO$ catalyst.

However, these procedures are not ideal in that they suffer from drawbacks such as the expense of the catalysts, cumbersome use of catalyst layers, difficulty in preparing catalysts, and poor selectivity to desired products.

More recently, methylisobutylketone has been made in Germany and Russia by a one-step process using a palladium on cation-exchange resin as the catalyst, Takaoka, S. SRI Process Economic Program-Report No. 77 (May 1972); (b) Askew, W. S., ibid. Review No. 81-1-2 (November 1981). This process also suffers from several drawbacks. It can only utilize acetone to produce methylisobutylketone, and it cannot produce methylisobutylcarbinol. An expensive palladium on cation-exchange resin catalyst is required, with a limited lifetime. In addition, this process cannot be operated above 130° C., as the palladium catalyst is not thermally stable above this temperature.

SUMMARY OF THE INVENTION

The present invention provides a novel process for preparing a product ketone compound of the general formula:

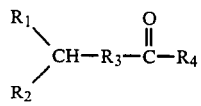

which comprises contacting at least one starting compound of the general Formula I:

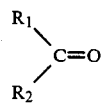

Formula I with a catalytically effective amount of a catalyst comprising copper oxide, in the presence of hydrogen, at a selective temperature in the range of about 200° C. to about 500° C., wherein $R_1$ and $R_2$ are the same or different and are H or an alkyl group, provided $R_1$ and $R_2$ are not both H; $R_3$ is a methylene or alkyl substituted methylene group derived from $R_1$ or $R_2$; and $R_4$ is $R_1$ or $R_2$.

The present invention also provides a novel process for the production of a product carbinol of the general formula:

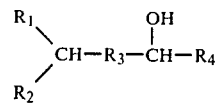

which comprises contacting the product ketone as described above with a catalytically effective amount of a catalyst comprising copper oxide, in the presence of hydrogen, at a selective temperature in the range of about 50° C. to about 350° C., wherein $R_1$ and $R_2$ are the same or different and are H or an alkyl group, provided $R_1$ and $R_2$ are not both H; $R_3$ is a methylene or alkyl substituted methylene group derived from $R_1$ or $R_2$; and $R_4$ is $R_1$ or $R_2$.

DETAILED DESCRIPTION OF THE INVENTION

In the process of this invention, at least one compound of general Formula I, or a compound capable of forming such a compound in situ is contacted with a "catalytically effective" amount of a first catalyst comprising copper oxide, in the presence of hydrogen, to produce an aliphatic ketone. The starting reactants can vary widely and may be a first compound of the general Formula I, or a precursor capable of forming a compound of Formula I and hydrogen in situ such as an alcohol of the general formula II:

Starting reactants of the general Formula I or II are particularly useful wherein $R_1$ is H or an alkyl of from about 1–18 carbon atoms and $R_2$ is the same or a different alkyl of from about 1–18 carbon atoms. It is particularly preferred that $R_1$ and $R_2$ be the same or a different alkyl from about 1–8 carbon atoms, more preferred being the same or different alkyls from about 1–4 carbon atoms, and most preferred the same alkyl group of about 1–4 carbon atoms.

Illustrative of particularly useful starting reactants of Formula I are compounds such as acetone, acetaldehyde, 2-butanone, propanaldehyde, 2-pentanone, 3-pentanone, butyraldehyde, 2-hexanone, 3-hexanone, pentanaldehyde, 3-methyl, 2-butanone, pinacolone, and the like. Illustrative of precursor starting reactants of Formula II are those such as isopropanol, 2-butanol, 2-pentanol, 3-pentanol, 2-hexanol, 3-hexanol, 3-methyl 2-butanol, 2,2-dimethyl 2-butanol, and the like. Preferred among the latter are isopropyl alcohol, 2-butanol, and 2-pentanol, which convert in situ into acetone, 2-butanone, and 2-pentanone, respectively, and hydrogen. Most preferred of the starting compounds from those listed above are acetone, 2-butanone, and acetaldehyde, and the corresponding compounds capable of converting to these and hydrogen in situ under the process conditions of the present invention.

A supply of hydrogen is required to effect the conversion of the starting materials to the desired product. If not present, the reaction will stop at an intermediate, such as mesityl oxide. This source of hydrogen may be provided externally or internally. When aliphatic ketones or aldehydes are employed as the starting material, an external source of hydrogen should be supplied, preferably in the form of a gas. Any convenient manner of supplying the hydrogen may be effected, and it is not required that the hydrogen be in pure form. For example, Syn gas ($CO+H_2$) may be used in place of pure hydrogen, and mixtures of carbon dioxide, carbon monoxide, water and hydrogen from Shift Gas reaction are also suitable.

The amount of hydrogen necessary varies widely and is governed to an extent by reactant proportions, reaction parameters such as time, temperature, pressure, and equipment used in the process, and the like. In general, the amount required is that which will produce the saturated product ketone to any extent. However, in most cases it is preferred to employ at least a stoichiometric amount of hydrogen, and more preferred to employ an excess of hydrogen. Thus, suitable ratios of hydrogen to starting ketone reactant can range in general from about one to one to about three to one.

When alcohols are employed as precursors for the starting materials, they are converted in situ to a ketone and hydrogen. Thus an internal source of hydrogen is provided in situ upon the formation of this first ketone from the alcohol. Accordingly, an outside source of hydrogen is not required, although one may add additional hydrogen as discussed above to insure the complete reduction of olefinic intermediates in the reaction.

Combination to any extent of one or more compounds of general Formula I with one or more from general Formula II as described above is also within the contemplation of the present invention, as long as hydrogen is provided externally, or internally by the starting reactant itself, as discussed above. A combination of a ketone and an alcohol having similar $R_1$ and $R_2$ substituents is preferred.

It is particularly preferred to combine isopropanol and acetone for use as starting material. In this case, any amount of isopropanol may be combined with the acetone as long as hydrogen is present for the reaction. It is preferred, however, that there be a greater quantity of isopropanol, as it is this compound tht provides the internal source of hydrogen. Preferred ratios of the isopropanol to acetone are from about 10 to about 1, more preferred ratios are about 5 to about 1. The most preferred ratio of isopropanol to acetone is about 1 to about 1, as a sufficient amount of hydrogen is produced by the isopropanol when it splits into acetone and hydrogen to accomodate the hydrogen requirements for purposes of the final conversion to an aliphatic ketone.

The catalyst of the present invention is one that contains any amount of copper oxide (CuO) sufficient to catalyze the conversion of the starting materials to produce ketones or carbinols. The copper oxide may be in cuprous or cupric form or a mixture thereof, however, it is preferred that it be in the cupric form.

Preferred percentages of copper oxide range from about 10% to about 80%, particularly preferred being about 40% to about 70%, with about 59% to about 61% most preferred. It is also preferred that the catalyst be provided a support to insure that an adequate amount of surface area will be available to effect catalysis. Such support materials may vary widely, a preferred support or binder material for this purpose being alumina. Other suitable materials may also be used such as zinc oxide, magnesia, zirconia, titania, boric acid treated clays, combinations of the above materials, and the like. When alumina is used, preferred percentages range from about 5% to about 90%, with about 9% to about 11% being particularly preferred.

The copper oxide does not have to be present in pure form, as other components may be provided in the catalyst. In some preferred embodiments, zinc oxide is present in amounts of about 1% to about 47%, with about 29% to about 31% particularly preferred. A particularly preferred catalyst for use in the present process is that referred to in the art as the "methanol synthesis catalyst," with percentages of components generally of about 60% copper oxide, alumina about 10%, and zinc oxide about 30%.

The process is carried out in the presence of a "catalytically effective amount" of the catalyst described above. As used herein, "a catalytically effective amount" is an amount of the catalyst which is sufficient to catalyze the reaction to produce the desired products to any extent, and preferably to an extent of at least about 50%. As one skilled in the art will readily appreciate, determination of an amount of catalyst will depend on whether the reaction is conducted in a continuous fashion or a batch fashion.

With respect to the continuous mode of operation, it is preferred to use a fixed bed system, wherein the catalyst in a powdered form is packed into a tube and the reactants run past it. One skilled in the art will appreciate that in this case, the catalytic process is a surface phenomenon, and thus an appreciable amount of catalytic surface is often desirable. In a conventional fixed bed system, catalyst in a powdered form may be packed into an area of pyrolysis tubing that varies in length and diameter. In such tubing having a diameter of less than about 1 inch and a length of less than about 5 inches, it is preferred to pack about 4 grams to about 20 grams of catalyst, more preferably about 4 to about 10 grams, most preferably about 6 grams to about 10 grams. It is generally expected that the catalytic surface area would be such that conversions of about 50% to about 90% per pass can be effected in this manner.

When the process is carried out in a batch fashion, the amount of catalyst employed is generally at least about 0.1 mole percent based on the total moles of starting material, and in the particularly preferred embodiments the amount of catalyst may vary from about 0.5 to about 15 mole percent on the aforementioned basis. Amongst these particularly preferred embodiments, most preferred are those embodiments in which the mole percent of catalyst various from about 1 to 10 mole percent based on the total moles of starting material.

In order to maintain the activity of the catalyst of the present invention over a long period of time, it is preferred to provide a supply of $CO_2$ to some extent, preferably having it present at all times during the reaction. This may be accomplished by any conventional means such as carrying out the reaction in an atmosphere of $CO_2$. The $CO_2$ does not have to be in pure form, but may be mixtures of $CO_2$ and CO, $H_2O$, and the like. For example, in a continuous reaction, preferred amounts of $CO_2$ may be added to the reaction as a gas or mixture of gases ranging from about 50 ml/min to about 150 ml/min, with about 90 ml/min to about 110 ml/min particularly preferred. The $CO_2$ exiting from the reactor may be recycled without purification.

The amount of starting reactants employed is dependent upon the desired amount of product ketones. Excellent conversion of starting reactant to product can be expected following the process steps as herein defined.

At optimal reaction parameters for example, conversion that ranges from about 25%, to as high as about 99% can be achieved, without conversion back to starting compounds.

Percent conversion of reactants into the desired aliphatic ketone products is temperature dependent. To achieve maximum formation of and selectivity to product aliphatic ketones from the starting material, it is preferable to carry out the reaction at temperatures above about 250° C., particularly from about 250° C. to about 1000° C., more preferably from about 350° C.–500° C., most preferably from about 380° C. to about 420° C. Temperatures below about 250° C. tend to result in a mixture of product ketones with intermediates in the reaction scheme and other compounds such as carbinols and the like, necessitating additional purification processes to obtain the product ketone. However, in some cases a mixture may be desired, and hence one may achieve it by adjusting the reaction temperature in this manner.

the reaction may be carried out at atmospheric or superatmospheric pressures. It is preferred to operate at superatmospheric pressures however, to facilitate contact of the hydrogen gas with the other reactants. Superatmospheric pressures useful in the process of the invention may vary widely and are influenced by reaction time and temperatures. In general, it is desirable to conduct the process below about 200 psig. A preferred range is that of about 50 psig to about 150 psig; with about 95 psig to about 105 psig most preferred.

The process of this invention is carried out over a period of time sufficient to produce the desired compound in adequate yield. Reaction times are influenced to a significant degree by the reaction temperature, concentration and choice of reactants, and by other factors known to those skilled in the art. In general, when effecting pyrolysis, residence times of the reactants can vary from about a few seconds to 2 minutes or longer. In most instances, when employing preferred reaction conditions, residence times will be found to vary from about 10 seconds to about 1 minute.

The process of the invention may be carried out in any suitable pyrolysis apparatus, such as a fluidized bed reactor or tubular reactor, or the like. If tube construction is employed, the diameter of the tube should be such that there is a high surface to volume ratio and long length to promote effective heat transfer. To insure that the temperature remains constant, it may be monitored along the length of the reactor. This may be accomplished by attaching thermocouples to the walls of a reactor vessel, within the reactor itself, or by an other suitable design to accomplish this purpose.

The process of this invention can be conducted in a batch, semicontinuous or continuous fashion. The reactants and reagents may be initially introduced into the reaction zone batchwise or they may be continuously or intermittently introduced in such zone during the course of the process. Means to introduce and/or adjust the quantity of reactants introduced, either intermittently or continuously into the reaction zone during the course of the reaction can be conveniently utilized in the process, especially to maintain the desired molar ratio of reactants. The reaction can be conducted in a single reaction zone or in a plurality of reaction zones, in series or in parallel or it may be conducted intermittently or continuously in an elongated tubular zone or series of such zones.

The materials of construction employed should be inert to the reactants during the reaction and the fabrication of the equipment should be able to withstand the reaction temperatures and pressure. The reaction zone can also be fitted with one or more internal and/or external heat exchanger's in order to control undue temperature fluctuations, or to prevent any possible undesirably elevated reaction temperatures.

In some embodiments of the process, agitation means to vary the degree of mixing of the reaction mixture can be employed. Mixing by vibration, shaking, stirring, rotation, oscillation, ultrasonic vibration or the like are all illustrative of the type of agitation means contemplated. Such means are available and well known to those skilled in the art.

After the conversion to produce aliphatic ketones is effected, the product may be condensed from the reaction mixture by any suitable condensation technique, such as water cooling, ice bath cooling, dry ice acetone cooling, and the like, and may be further purified employing conventional techniques. Illustrative of such purification techniques are evaporation, distillation, solvent extraction and recrystallization. The preferred purification technique is distillation.

Alternatively, at least a portion of the product aliphatic ketones may be subjected to a second conversion, producing a product carbinol as described above. In this case, the product aliphatic ketone is further processed as a starting reactant in the presence of a source of hydrogen, selectively producing the carbinol. The product aliphatic ketoned does not have to be in pure form and may contain other components that do not interfere with this second reaction, or may even be mixed with an outside source of ketones or combinations thereof.

The various reaction parameters and types of catalysts detailed above for the production of the aliphatic ketones are equally applicable to the second stage production of the corresponding carbinols with the exception of the temperatures employed in this second reaction. The preferred temperature range to effect the conversion of aliphatic ketones in the presence of hydrogen to carbinols is below about 350° C., preferably below about 250° C., more preferably between about 250° C. and about 100° C., most preferably between about 175° C. and 100° C.

Any suitable apparatus design as described above may also be employed to effect the subsequent conversion of the product aliphatic ketones to carbinols. For example, the ketones may be collected and they recycled through the same reaction zone at temperatures favoring the conversion to carbinols. A second reaction zone in proximity to the first may also be employed, containing a similar or identical catalyst. Alternatively, of course, one may wish to store the product ketones for further conversion at a later date in the same or a similar pyrolysis apparatus.

DETAILED DESCRIPTION OF THE PREFERRED EMBODIMENTS

In a preferred embodiment in the present invention, isopropanol or a mixture of isopropanol and acetone or a mixture of acetone and hydrogen is converted to form methylisobutylketone (MIBK), which can be further converted to methylisobutylcarbinol (MIBC) to the extent desired. By way of illustration, the following are the proposed chemical reaction steps for this conversion scheme:

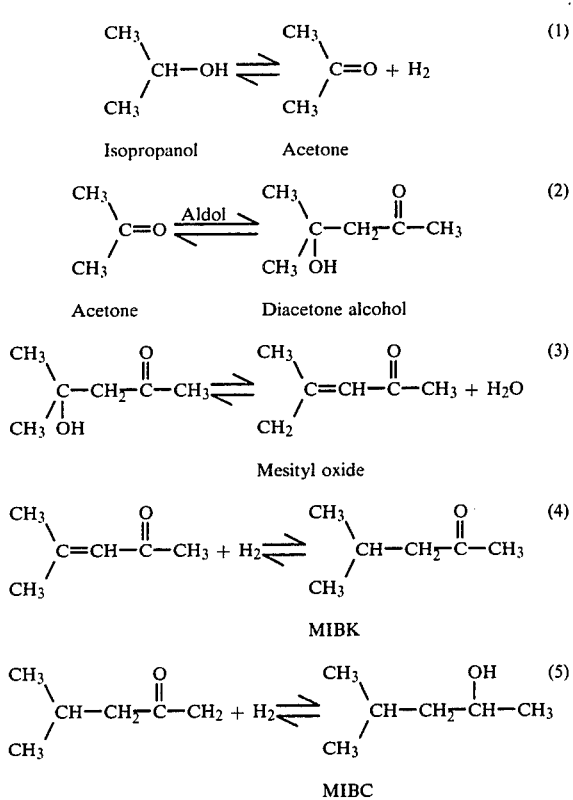

Steps 1 to 4 are thermodynamically favored above 400° C. Step 5 is not favored at this temperature. Thus, starting with isopropanol (Ip), or an equimolar mixture of isopropanol and acetone (Ac), or acetone and hydrogen as feedstock, the conversion of the three-carbon feedstock is respectively 58%, 50% and 45%. The reaction product is predominently made of acetone and MIBK. At 400° C., MIBC is not observed at all in the reaction product. The amounts of isopropanol and mesityl oxide (MO) formed are small. Small amounts of diisobutylketone (DIBK) (derived from MIBK and acetone) are also observed.

diisobutylketone formed from the MIBK, acetone and hydrogen.

A mixture of MIBC and MIBK may be simultaneously produced at the onset by adjusting the reaction temperature to below about 250° C. However, further processes will have to be employed to separate the two compounds from the resulting product mixture.

As demonstrated by entries 4 and 5 in Table 1, at about 130° C., the conversion of the three-carbon feedstock starting from acetone and hydrogen is 16.4% and from isopropanol is 8.6%. Isopropanol becomes the major reaction product, while MIBC predominates over MIBK in the aldol product. Small amounts of mesityl oxide are also seen, however, no diisobutylketone is formed. Thus, 130° C. favors secondary alcohols over ketones and the conversion of three-carbon feedstock to aldol products is poor.

The following are specific examples that more particularly define certain aspects of the present invention but should not be considered limitative thereof.

EXAMPLE 1

A stainless steel tube (13"×⅜" I.D.) was used as a flow reactor. It was heated by means of an electric furnace controlled by West #400 Temperature Controller. Eight grams of the methanol synthesis catalyst (C79-2 supplied by United Catalyst-Inc. containing 60% CuO, 30% ZnO and 10% $Al_2O_3$) was packed in the reactor tube to a length of 3.3". The catalyst was roughly 20-60 mesh size. Three thermocouples were used to monitor the temperature of the furnace and the catalyst bed at the entry and exit points. Gases were introduced into the reactor using stainless steel tubing (1/16" O.D.). Gas flow rates were measured and controlled by the Tylan gas-flow system. The liquid reactants were delivered into the reactor at the same entry point as the gases using a Milton Ray minipump by means of a stainless steel tubing (1/16" O.D.). Before introducing the reactants, the reactor was heated at 400° C. for 30 minutes under a current of carbon dioxide (100 ml/min) in order to preserve the activity of the catalyst. The reactor pressure was controlled by a Grove-Valve and the pressure was measured using a pressure gauge.

TABLE 1

| No. | Reactor Feed (gmol/hr) | Reactor Condition | % Conversion | Steady State Composition of Products (mol %) | | | | | |
|---|---|---|---|---|---|---|---|---|---|
| | | | | Ac | Ip | MIBK | MIBC | MO | DIBK |
| 1. | Ispropanol (0.23) | 400° C. 100 psig | 58 | 56.5 | 3.4 | 36.2 | 0.0 | 1.3 | 2.4 |
| 2. | Isopropanol Acetone (0.28) | 400° C. 90 psig | 50 | 65.5 | 2.0 | 29.7 | 0.0 | 1.4 | 1.8 |
| 3. | Acetone + $H_2$ (0.33) (0.13) | 400° C. 100 psig | 45 | 70.5 | 1.1 | 25.4 | 0.0 | 1.5 | 1.5 |
| 4. | Acetone + $H_2$ (0.27) (0.33) | 130° C. | 16.4 | 17.1 | 74.0 | 1.8 | 6.7 | 0.4 | 0.0 |
| 5. | Isopropanol (0.23) | 130° C. 100 psig | 8.6 | 14.3 | 81.2 | 0.7 | 3.6 | 0.2 | 0.0 |
| 6. | MIBK + $H_2$ (0.24) (0.33) | 150° C. 100 psig | 96 | 0.0 | 0.0 | 3.6 | 96.0 | 0.0 | 0.0 |

From entries 1, 2 and 3 in Table 1, it is clear that at 400° C., formation of ketones is favored over secondary alcohols. MIBC is not observed at all. The amount of isopropanol observed in this reaction product is small, and is generally expected to be recycled along with the unreacted acetone. Reduction of mesityl oxide to MIBK may not be complete, and accordingly, small amounts of mesityl oxide can often be observed in the reaction product, along with the small amounts of Acetone was pumped into the reactor at the rate of 0.33 gmol/hr. and hydrogen at the rate of 0.13 gmol/hr. The pressure of the reactor was maintained at 100 psig. The liquid products were condensed using a dry ice-acetone trap and analyzed using gas chromatography (Hewlett Packard 5710A), HNMR (Varian T-60) and in (Perkin-Elmer 128). Molecular weights were determined by a Finnigan gc-mass spectrometer. Gaseous products were analyzed by gas chromatography.

The steady-state composition of the liquid products (in mol. %) are as follows: acetone (70.5), isopropanol (1.1), methylisobutyketone (25.4), mesityloxide (1.5) and diisobutylketone (1.5). Methylisobutylcarbinol was not observed. The gaseous products were carbon dioxide, carbon monoxide, hydrogen and traces of water, acetone and isopropanol. The overall conversion of the three-carbon feedstock was of the order of 45% per pass. The residence time was approximately 27 sec. The reaction was run continuously 4 to 8 hours.

EXAMPLE 2

The reactor described in Example 1 was used. The catalyst was maintained under carbon dioxide (100 ml/min) at 400° C. and 100 psig pressure. Isopropanol was pumped into the reactor (0.23 gmol/hr.). An external source of hydrogen is not needed when isopropanol is the reactant. The steady-state composition of the liquid products (in mol. percent) was acetone (56.5), isopropanol (3.4), methylisobutylketone (36.2), mesityloxide (1.5) and diisobutylketone (2.4). Methylisobutylcarbinol was not observed. The overall conversion of the three-carbon feedstock was of the order of 58%. A residence time of 18 sec. was calculated. The reaction was continuously run 4 to 8 hours.

EXAMPLE 3

The reactor described in Example 1 was used. The catalyst was maintained under carbon dioxide (100 ml/hr.) at 400° C. and 100 psig pressure. An equimolar mixture of acetone and isopropanol was pumped into the reactor (0.28 gmol/hr.). As in Example 2, an external source of hydrogen was not needed. The steady-state composition of the liquid products (in mol. percent) was as follows: acetone (65.1), isopropanol (2.0), methylisobutylketone (29.7), mesityloxide (1.4) and diisobutylketone (1.8). Methylisobutylcarbinol was not observed. The overall conversion of the three-carbon feedstock was of the order of 50.2%. The reaction was continuously run 4 to 8 hours.

EXAMPLE 4

The experiment described in Example 1 was repeated except for the following changes. The reaction was run at 130° C. and acetone and hydrogen were fed into the reactor at the rate of 0.27 gmol/hr. and 0.33 gmol/hr. respectively. The steady-state composition of the liquid products (in mol percent) was as follows: acetone (17.1), isopropanol (74.0), Methylisobutylketone (1.8), methylisobutylcarbinol (6.7) and mesityloxide (0.4). The overall conversion of the three-carbon feedstock was 16.4%. The reaction was continuously run 4 to 8 hours. This demonstrates poor conversion to MIBK under the temperatures employed.

EXAMPLE 5

The experiment described in Example 2 was repeated at 130° C., to further demonstrate the criticality of temperature in the conversion of starting reactants to product aliphatic ketones. The steady-state composition (in mol. percent) of the liquid product after 4 hours was as follows: acetone (14.3) isopropanol (81.2), methylisobutylketone (0.7), methylisobutylcarbinol (3.6) and mesityloxide (0.2). The overall conversion of the three-carbon feedstock was 8.6%. The reaction was continuously run 4-8 hours. This supports the findings in Example 4.

EXAMPLE 6

The reactor described in Example 1 was used. The catalyst was maintained at 150° C. under carbon dioxide (100 ml/min.) at 100 psig. Methylisobutylketone and hydrogen were fed into the reactor at the rate of 0.24 gmol/hr. and 0.33 gmol/hr. respectively. The liquid product was made up of 96–99% methylisobutylcarbinol, about 0.2% 2-methylpentane and the rest methylisobutylketone. The residence was calculated to be 15 sec. The reaction was continuously run for 6 hours. This demonstrates the excellent selective conversion of MIBK to MIBC following the process parameters of the invention.

EXAMPLE 7

The experiment described in Example 6 was repeated at 330° C., to demonstrate the criticality of the lower temperature range in producing carbinols. Methylisobutylketone was introduced at the rate of 0.18 gmol/hr. and hydrogen was passed at the rate of 0.33 gmol/hr. Poor conversion was obtained as the product was mostly methylisobutylketone (77.7%). Methylisobutylcarbinol was formed only to an extent of 20.6%. 2-Methylpentane was also observed (1.7%). The reaction was continuously run for three hours.

EXAMPLE 8

Using the reactor and catalyst described in Example 1, cyclohexanol (fed at the rate of 0.12 gmol/hr.) was converted at 305° C. and atmospheric pressure to cyclohexanone (85.7%), cyclohexene (6.6%), cyclohexenone (2.9%) and phenol (0.7%). Aldol condensation products were not observed. The reaction was continuously run for 5 hours. This demonstrates that cyclic starting reactants do not result in the expected products when subjected to the process of the present invention.

EXAMPLE 9

The reactor described in Example 1 was used. Butyrophenone and hydrogen were fed into the reactor at the rate of 0.14 gmol/hr. and 0.33 gmol/hr. respectively. The reactor was heated at 151° C. under 100 psig pressure, and the reaction continuously run for 4 hours. Butyrophenone was completely converted to butylbenzene (96.3%) and 1-phenyl-1-butanol (3.7%). This demonstrates that aromatic ketones do not result in the expected products when subjected to the process of the present invention.

EXAMPLE 10

The reaction described in Example 9 was repeated at a lower temperature of 108° C. Butyrophenone was converted to an extent of 60% to 1-phenyl-1-butanol. Only trace amounts of butlybenzene were observed. The reaction was continuously run for three hours. Thus, lowering of the temperature did not help to achieve the expected products.

EXAMPLE 11

Experiments described in Example 1, 2, and 3 were repeated using the catalyst (C18-HC—Supplied by the United Catalyst Inc.) containing 42% CuO, 47% ZnO and 10% $Al_2O_3$. The steady-state composition of products in mol. percent after a 4-hour run was as follows: Acetone (50–71%), isopropanol (2–4%), methylisobutylketone (22–33%), mesityl oxide (about 1%) and diisobutylketone (about 1.5%).

EXAMPLE 12

The reaction described in Example 1 was repeated using the Harshaw T-317 catalyst containing 10% CuO and 90% $Al_2O_3$. The steady-state composition of products in mol. percent after a 4-hour run was as follows: acetone (51%), isopropanol (12%), methylisobutlketone (25%) methylisobutylcarbinol (0.5%) and disobutylketone (11.5%).

What is claimed is:

1. A process for preparing a product ketone compound of the general formula:

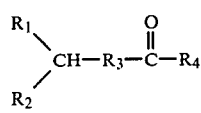

which comprises contacting a starting compound of the general Formula I:

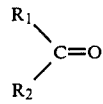

with a catalytically effective amount of a catalyst at least about 10% comprising copper oxide, in the presence of hydrogen, at a selective temperature in the range of about 250° C. to about 500° C. wherein, $R_1$ and $R_2$ are the same or different and are H or an alkyl group, provided that $R_1$ and $R_2$ are not both H;

$R_3$ is a methylene or alkyl substituted methylene group derived from $R_1$ or $R_2$; and $R_4$ is $R_1$ or $R_2$.

2. The process of claim 1 wherein $R_1$ is H and $R_2$ is an alkyl group of about 1–8 carbon atoms.

3. The process of claim 2 wherein $R_2$ is an alkyl group of about 1–4 carbon atoms.

4. The process of claim 1 wherein $R_1$ and $R_2$ are the same or different and are an alkyl group of about 1–14 carbon atoms.

5. The process of claim 4 wherein $R_1$ and $R_2$ are the same.

6. The process of claim 1 wherein the temperature is in the range of from about 350° C. to about 450° C.

7. The process of claim 1 wherein the starting compound is acetone.

8. The process of claim 1 wherein the ratio of hydrogen gas to acetone is about three to about one.

9. The process of claim 1 wherein said starting compound is produced in situ from a precursor of the general Formula II:

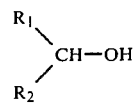

wherein,
$R_1$ is H or an alkyl group; and
$R_2$ is an alkyl group and is the same or different from $R_1$.

10. The process of claim 7 wherein the starting compound is produced in situ from isopropanol.

11. The process of claim 1 wherein the starting compound and a compound of general Formula II are contacted with the catalyst, said compound of general Formula II being a precursor of the starting compound.

12. The process of claim 11 wherein the starting compound is acetone and the compound of general Formula II is isopropanol.

13. The process of claim 12 wherein the ratio of isopropanol to acetone is about 1:1.

14. The process of claim 1 conducted at a pressure of about 50 psig to about 250 psig.

15. The process of claim 1 conducted at a pressure of about 50 psig to about 120 psig.

16. The process of claim 1 conducted in the presence of a source of $CO_2$.

17. The process of claim 1 wherein the catalyst comprises cupric oxide.

18. The process of claim 1 wherein the catalyst further comprises ZnO and $Al_2O_3$.

19. The process of claim 17 wherein the catalyst further comprises ZnO and $Al_2O_3$.

20. The process of claim 1 further comprising the step of contacting said product ketone compound with an effective amount of said catalyst, in the presence of hydrogen, at a selective temperature in the range of about 100° C. to about 250° C. to produce a carbinol compound of the general formula:

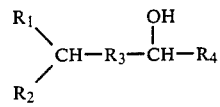

wherein,
$R_1$ and $R_2$ are the same or different and are H or an alkyl group, provided $R_1$ and $R_2$ are not both H;
$R_3$ is a methylene or alkyl substituted methylene group derived from $R_1$ or $R_2$; and
$R_4$ is $R_1$ or $R_2$.

* * * * *

UNITED STATES PATENT AND TRADEMARK OFFICE
CERTIFICATE OF CORRECTION

PATENT NO. : 4,704,480
DATED : November 3, 1987
INVENTOR(S) : F.J. Gefri et al.

It is certified that error appears in the above-identified patent and that said Letters Patent are hereby corrected as shown below:

Col. 5, line 21: "the" should read -- The --.

Col. 6, line 31: "ketoned" should read --ketone --.

line 50: "they" should read -- then --.

Col. 11, line 30-31: "with a catalytically effective amount of a catalyst at least about 10% comprising copper oxide, in the pres-"

should read -- with a catalytically effective amount of a catalyst comprising at least about 10% copper oxide, in the pres- --.

line 46: "1-14" should read -- 1-4 --.

Signed and Sealed this

Thirtieth Day of August, 1988

Attest:

DONALD J. QUIGG

*Attesting Officer*                    *Commissioner of Patents and Trademarks*